United States Patent
Taniguchi et al.

(10) Patent No.: US 12,089,921 B2
(45) Date of Patent: Sep. 17, 2024

(54) MAGNETIC RESONANCE IMAGING APPARATUS AND IMAGE PROCESSING METHOD

(71) Applicant: FUJIFILM Healthcare Corporation, Kashiwa (JP)

(72) Inventors: Yo Taniguchi, Chiba (JP); Toru Shirai, Chiba (JP)

(73) Assignee: FUJIFILM Healthcare Corporation, Chiba (JP)

( * ) Notice: Subject to any disclaimer, the term of this patent is extended or adjusted under 35 U.S.C. 154(b) by 0 days.

(21) Appl. No.: 17/573,729

(22) Filed: Jan. 12, 2022

(65) Prior Publication Data

US 2022/0240805 A1    Aug. 4, 2022

(30) Foreign Application Priority Data

Feb. 2, 2021    (JP) .................. 2021-015266

(51) Int. Cl.
*A61B 5/055*    (2006.01)
*G01R 33/54*    (2006.01)
*G06T 7/00*    (2017.01)

(52) U.S. Cl.
CPC ............ *A61B 5/055* (2013.01); *G01R 33/543* (2013.01); *G06T 7/0012* (2013.01); *G06T 2207/10088* (2013.01)

(58) Field of Classification Search
CPC .... A61B 5/055; G01R 33/543; G06T 7/0012; G06T 2207/10088
See application file for complete search history.

(56) References Cited

U.S. PATENT DOCUMENTS

| | | | |
|---|---|---|---|
| 2008/0199063 A1* | 8/2008 | O'Halloran | G01R 33/56341 382/131 |
| 2012/0319689 A1* | 12/2012 | Ichinose | G01R 33/3664 324/322 |
| 2013/0207654 A1* | 8/2013 | Takizawa | G01R 33/56572 324/318 |
| 2013/0265045 A1* | 10/2013 | Xu | G01R 33/56383 324/309 |
| 2017/0209067 A1* | 7/2017 | Taniguchi | G01R 33/387 |
| 2019/0213761 A1* | 7/2019 | Rosen | A61B 5/055 |
| 2019/0378271 A1* | 12/2019 | Takeshima | G16H 30/00 |
| 2020/0069214 A1* | 3/2020 | Takeshima | G01R 33/565 |
| 2020/0202586 A1* | 6/2020 | Li | G01R 33/5608 |
| 2020/0279413 A1* | 9/2020 | Wheaton | G06T 7/0002 |

FOREIGN PATENT DOCUMENTS

JP    2011-024926 A    2/2011

* cited by examiner

*Primary Examiner* — Dixomara Vargas
(74) *Attorney, Agent, or Firm* — Paul Teng (57) ABSTRACT

To provide a technique of stably obtaining quantitative parameter maps by preventing influences of artifacts caused by flow or body motion when calculated images with a plurality of parameters are generated at the same time. When a calculated image of a subject parameter or an apparatus parameter is generated by using a plurality of images obtained by performing imaging under different imaging conditions, an imaging condition under which the artifacts are easy to occur is examined in advance, and an imaging parameter set for quantitative parameter map calculation is optimized by excluding the imaging condition under which the artifact is easy to occur.

11 Claims, 11 Drawing Sheets

|     | T1 [ms] | T2 [ms] |
|-----|---------|---------|
| GM  | 1500    | 100     |
| WM  | 850     | 75      |
| fat | 300     | 70      |
| CSF | 3000    | 1200    |

MAGNETIC RESONANCE IMAGING APPARATUS AND IMAGE PROCESSING METHOD

BACKGROUND OF THE INVENTION

1. Field of the Invention

The present invention relates to a magnetic resonance imaging technique, in particular, to a method of estimating a subject parameter by calculation.

2. Description of the Related Art

A magnetic resonance imaging (MRI) apparatus is a medical image diagnostic apparatus that causes nuclear magnetic resonance in a hydrogen nucleus in any plane crossing a subject and captures a tomographic image in the plane based on a generated nuclear magnetic resonance signal. In general, a slice gradient magnetic field that specifies an imaging plane is applied, an excitation pulse (a radio frequency magnetic field pulse) that excites magnetization in the plane is applied at the same time, and a nuclear magnetic resonance signal (echo) generated at a stage where the magnetization excited in this manner converges is acquired. In order to give position information to the magnetization, a phase encoding gradient magnetic field and a readout gradient magnetic field in directions perpendicular to each other in a tomographic plane are applied during a period from the excitation to the acquisition of the echo.

The pulse for generating the echo and each gradient magnetic field pulses are applied based on a preset pulse sequence. Various pulse sequences are known depending on purposes. For example, a gradient echo (GE) type high-speed imaging method is a method including repeatedly operating the pulse sequence and sequentially measuring the number of echoes necessary for obtaining one tomographic image by sequentially changing the phase encoding gradient magnetic field for each repetition.

The MRI apparatus reconstructs an image of the subject by performing computation such as Fourier transform on the echo signal measured in this manner. A pixel value of the reconstructed image is determined by, in addition to properties of the subject itself, such as a proton density of the tissue, a longitudinal relaxation time T1, and a transverse relaxation time T2, imaging conditions (individual elements of the imaging conditions are referred to as imaging parameters) such as the type of the pulse sequence, the repetition time (TR) thereof, and the intensity and phase of the excitation pulse which is a radio frequency magnetic field pulse, and a condition related to the apparatus such as the magnetic field intensity. These elements that determine the pixel value are referred to as a subject parameter, an imaging parameter, and an apparatus parameter for the subject, the imaging condition, and the apparatus, respectively.

As described above, the reconstructed image itself does not represent values (quantitative values) of the subject parameters or the like. If a function (signal function) representing relations between the imaging parameter and the pixel value, between the subject parameter and the pixel value, between the apparatus parameter and the pixel value is known, the quantitative value can be estimated by calculation using the function and an image (calculation image) using the quantitative value as the pixel value can be obtained. The signal function depends on an imaging sequence. JP-A-2011-024926 proposes a method including obtaining a signal function by a numerical simulation, obtaining a least square fit of the signal function with respect to imaging parameters of a plurality of original images and pixel values thereof, and thereby calculating a calculation image in which a value of a subject parameter or an apparatus parameter is set as a pixel value.

In the method, in order to minimize a quantitative value estimation error between the subject parameter and the apparatus parameter, imaging conditions (imaging parameters) of the plurality of original images are determined using the law of error propagation. In optimization of the imaging parameters using the law of error propagation, a quantitative value estimation error with respect to the subject parameter or apparatus parameter, which is a target, is calculated for all combinations of given imaging parameters, and a combination by which the quantitative value estimation error is minimized is searched for.

In the process of determining the imaging parameter using the law of error propagation in JP-A-2011-024926, artifacts occurring in an image is not considered in a specific imaging parameter. Therefore, an imaging parameter that is likely to cause artifacts by the influence of a blood flow, a cerebrospinal fluid flow, a body motion, and the like may be selected. In this case, artifacts may occur in an original image so that artifacts may also occur in the subject parameter and the apparatus parameter calculated in consideration of the artifacts, or artifacts may act as noise to reduce an SN ratio. Since the artifacts caused by the flow or motion is not constant, a quantitative value may vary for each imaging.

SUMMARY OF THE INVENTION

The invention has been made in view of the above issues, and an object of the invention is to provide a technique of stably obtaining a quantitative value map while preventing the influence of artifacts caused by flow or body motion when a calculation image of a subject parameter or an apparatus parameter is generated.

The artifacts caused by the flow or body motion is different in ease of occurrence depending on the imaging condition. In the invention, an imaging condition under which the artifacts are easy to occur is examined in advance, and an imaging parameter set for quantitative value map calculation is optimized by excluding the imaging condition under which the artifacts is easy to occur.

Specifically, an MRI apparatus according to the invention includes: a measurement unit configured to measure, in accordance with a predetermined imaging condition and a predetermined imaging sequence, an echo signal generated from a subject placed in a static magnetic field by applying a radio frequency magnetic field and a gradient magnetic field to the subject; an image reconstruction unit configured to generate a reconstructed image based on the measured echo signal; a parameter estimation unit configured to estimate a distribution of subject parameters depending on the subject or a distribution of apparatus parameters depending on the apparatus by using reconstructed images obtained by executing the imaging sequence while changing the imaging condition and a signal function determined by the imaging sequence; and an imaging condition determination unit configured to determine a plurality of combinations of imaging conditions for obtaining a plurality of reconstructed images to be used by the parameter estimation unit. The imaging condition determination unit is configured to evaluate an image quality of the reconstructed image, includes an imaging condition searching unit configured to search for a combination of imaging conditions to be excluded from the plurality of combinations of imaging conditions, and is configured to determine the plurality of combinations of imaging conditions by excluding the combination of imaging conditions to be excluded.

The function of the imaging condition determination unit described above can be implemented by a main body of the MRI apparatus, but a part of the function can be implemented by an image processing apparatus different from the MRI apparatus.

In addition, an image processing method according to the invention is an image processing method of processing a plurality of reconstructed images obtained under different imaging conditions in an MRI apparatus and estimating a distribution of subject parameters depending on a subject or a distribution of apparatus parameters depending on the apparatus. The image processing method includes: evaluating an image quality of a reconstructed image under each imaging condition; and searching for an imaging condition to be used for parameter estimation to be performed by the MRI apparatus.

According to the invention, by determining the imaging parameters in consideration of the image quality of the reconstructed image obtained under each imaging condition (imaging parameter), optimization can be performed using only an imaging parameter that is less likely to cause artifacts. Accordingly, a quantitative value map can be stably obtained.

DESCRIPTION OF THE PREFERRED EMBODIMENTS

An embodiment to which the invention is applied will be described below. Hereinafter, in all the drawings for illustrating embodiments of the invention, components having the same functions are denoted by the same reference numerals, and repeated description thereof will be omitted.

Figure 1:
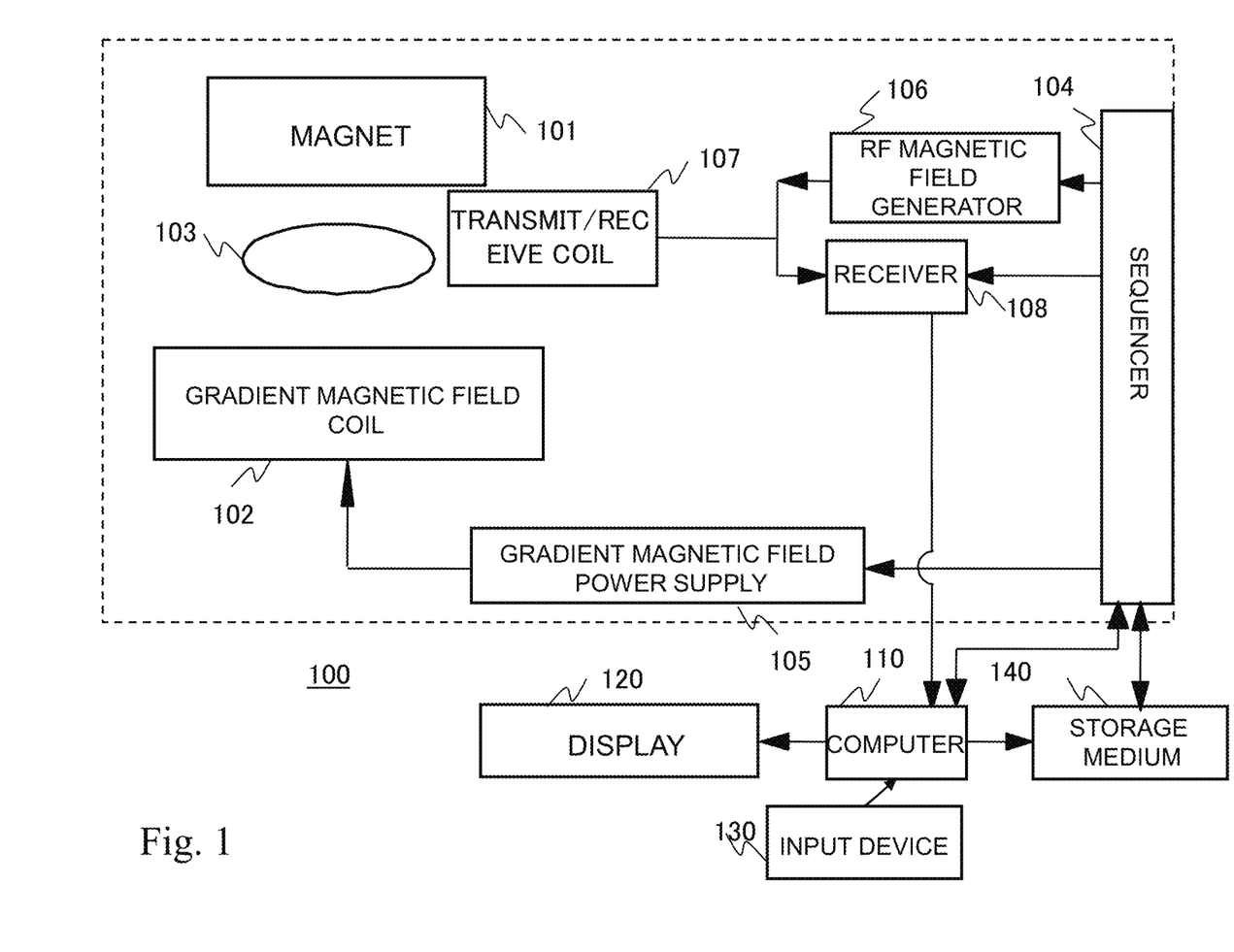
FIG. 1 is a block diagram showing a schematic configuration of an MRI apparatus according to an embodiment of the invention.

First, an MRI apparatus according to the present embodiment will be described. FIG. 1 is a block diagram showing a schematic configuration of an MRI apparatus 10 according to the present embodiment. The MRI apparatus 10 mainly includes a measurement unit 100 configured to measure an echo signal from a subject, which is a nuclear magnetic resonance signal, and a computer 110 configured to perform computation using the echo signal and to control the measurement unit 100. Devices attached to the computer 110 include a display 120, an input device 130, a storage medium 140, and the like.

The measurement unit 100 measures, in accordance with a predetermined imaging condition and a predetermined imaging sequence, an echo signal generated from a subject placed in a static magnetic field by applying a radio frequency magnetic field and a gradient magnetic field to the subject. The measurement unit 100 includes a magnet 101 for generating the static magnetic field, a gradient magnetic field coil 102 for generating the gradient magnetic field, a sequencer 104, a gradient magnetic field power supply 105, a radio frequency (RF) magnetic field generator 106, a transmit/receive coil 107 for irradiating the radio frequency magnetic field and detecting a nuclear magnetic resonance signal, and a receiver 108. Although a single transmit/receive coil 107 is shown in the drawing, a transmit coil and a receive coil may be separately provided. A subject (for example, a living body) 103 is placed and is imaged on a bed (table) in a static magnetic field space generated by the magnet 101.

The sequencer 104 generally controls each device to operate at timing and intensity programmed in advance. Among programs, in particular, a program in which timing and intensity of the radio frequency magnetic field, the gradient magnetic field, and timing of signal reception are recorded is called a pulse sequence. The sequencer 104 calculates an imaging sequence in accordance with a set pulse sequence and an imaging condition optionally set by a user, sends a command to the gradient magnetic field power supply 105 and the radio frequency magnetic field generator 106 in accordance with the imaging sequence, and generates a gradient magnetic field and a radio frequency magnetic field, respectively.

The radio frequency magnetic field generated by the radio frequency magnetic field generator 106 is applied to the subject 103 through the transmit/receive coil 107. The nuclear magnetic resonance signal generated from the subject 103 is received by the transmit/receive coil 107 and detected by the receiver 108. A nuclear magnetic resonance frequency (detection reference frequency f0) as a reference for detection is set by the sequencer 104. A detected signal is sent to the computer 110, where signal processing such as image reconstruction is performed. The result is displayed on the display 120. If necessary, the detected signal and the imaging condition can be stored in the storage medium 140.

Figure 2:
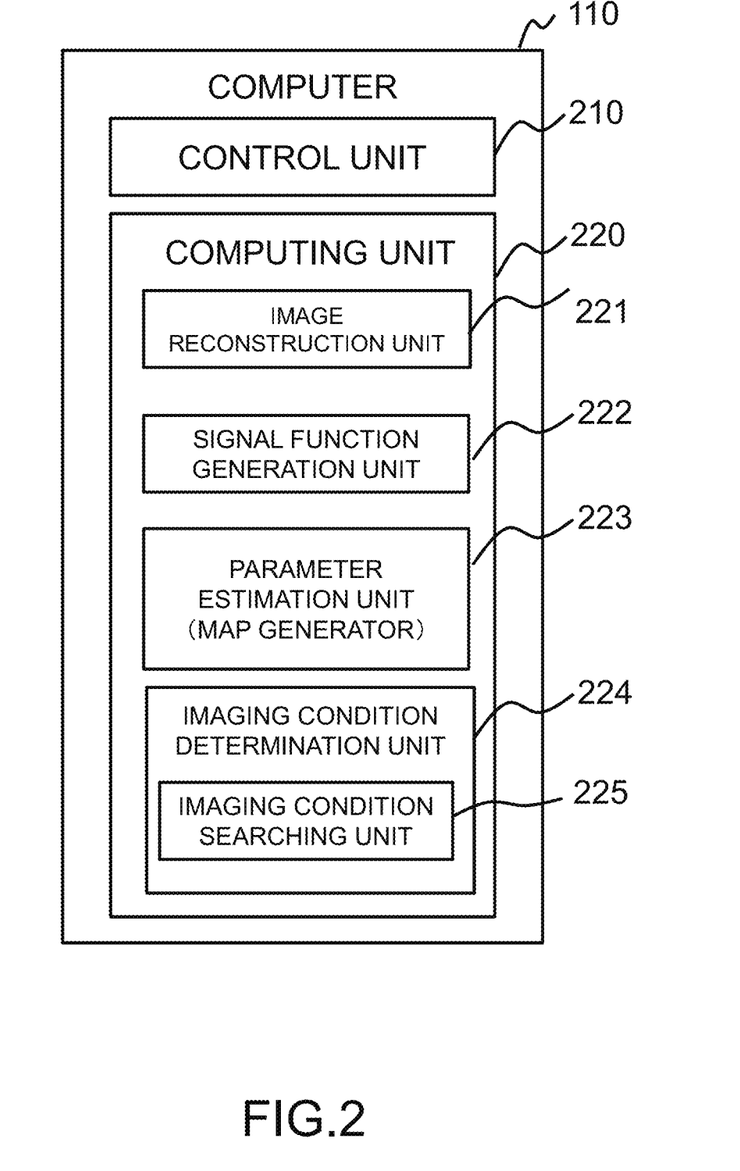
FIG. 2 is a functional block diagram of a computer according to the embodiment of the invention.

The computer 110 includes a CPU and a memory, controls an operation of each portion of the measurement unit 100, and performs various signal processing on the obtained echo signal to obtain a desired image. In order to perform the processing, as shown in FIG. 2, the computer 110 of the present embodiment includes a control unit 210 and a computing unit 220. Each function of the computer 110 is implemented by the CPU of the computer 110 loading a program stored in the storage medium 140 into the memory and executing the program.

The MRI apparatus of the present embodiment obtains a quantitative value using a signal function determined by the imaging sequence, and obtains a calculation image based on the obtained quantitative value. Thus, the computing unit 220 includes an image reconstruction unit 221 configured to obtain a reconstructed image based on the measured echo signal, a signal function generation unit 222 configured to generate a signal function for each imaging sequence by numerical simulation, a parameter estimation unit 223 configured to estimate a quantitative value (subject parameter or apparatus parameter) using the signal function for each imaging sequence and generate a calculation image (parameter image), and an imaging condition determination unit 224 configured to determine an imaging condition for parameter estimation. The imaging condition determination unit 224 includes an imaging condition searching unit 225 configured to search for an imaging condition to be excluded from a plurality of combinations of imaging conditions.

The subject parameter includes a longitudinal relaxation time (T1), a transverse relaxation time (T2), a spin density (ρ), a resonance frequency difference (Δf0), a diffusion coefficient (b), and an irradiation intensity distribution (B1) in a radio frequency magnetic field. The resonance frequency difference Δf0 is a difference between a resonance frequency of each pixel and the reference frequency f0. The apparatus parameter includes a static magnetic field intensity (B0) and a sensitivity distribution (Sc) of a reception coil. Here, the subject parameter and the apparatus parameter are collectively referred to as a quantitative value. In the present embodiment, a distribution of the quantitative value obtained for each pixel is referred to as a calculation image or a map.

A parameter that can be optionally set by the user at the time of execution of the imaging sequence is referred to as an imaging condition or an imaging parameter. The imaging condition includes, for example, a repetition time (TR), an echo time (TE), a set intensity of the radio frequency magnetic field (flip angle (FA)), and a phase of the radio frequency magnetic field (phase increment value θ).

A part of the functions of the computer 110 shown in FIG. 2 may be implemented by hardware such as a programmable logic device (PLD). The signal function generation unit 222 and the parameter estimation unit 223 can be built in a computer provided independently from the MRI apparatus 100, which is a computer capable of transmitting and receiving data to and from the computer 110 of the MRI apparatus 100.

Based on the above configuration, an embodiment of a processing to be performed by the MRI apparatus 10 of the present embodiment, mainly a processing related to parameter estimation will be described.

First Embodiment

In the present embodiment, a case where a combination of FA, TR, and θ is used as a parameter set as an imaging parameter, and estimation of the quantitative value (parameter estimation) is performed using a plurality of parameter sets having different values of one or more parameters constituting the parameter set will be described.

Figure 3:
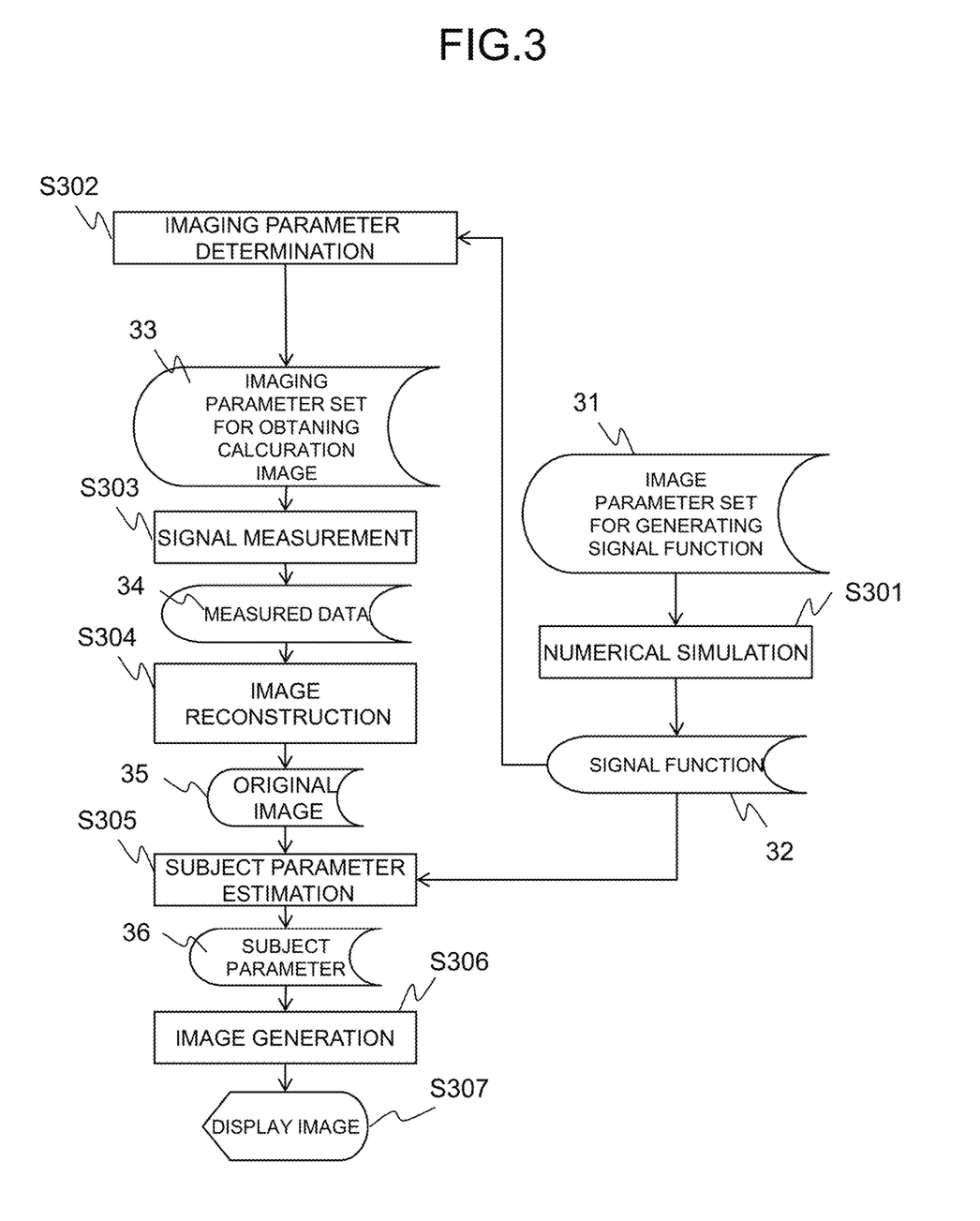
FIG. 3 is a processing flow according to the embodiment of the invention.

FIG. 3 shows a processing flow in the present embodiment. As shown in FIG. 3, generation of a signal function by numerical simulation (S301), determination of a plurality of imaging parameter sets performed by the imaging condition determination unit 224 (S302), signal measurement under conditions of the imaging parameter sets performed by the measurement unit 110 (S303), image reconstruction performed using measurement data performed by the image reconstruction unit 221 (S304), parameter estimation performed using the reconstructed image (original image) (S305), image generation performed using the estimated parameter (S306), and output of the image (S307) are performed.

Each step will be described in detail below.

[S301: Generation of Signal Function]

Figure 4A:
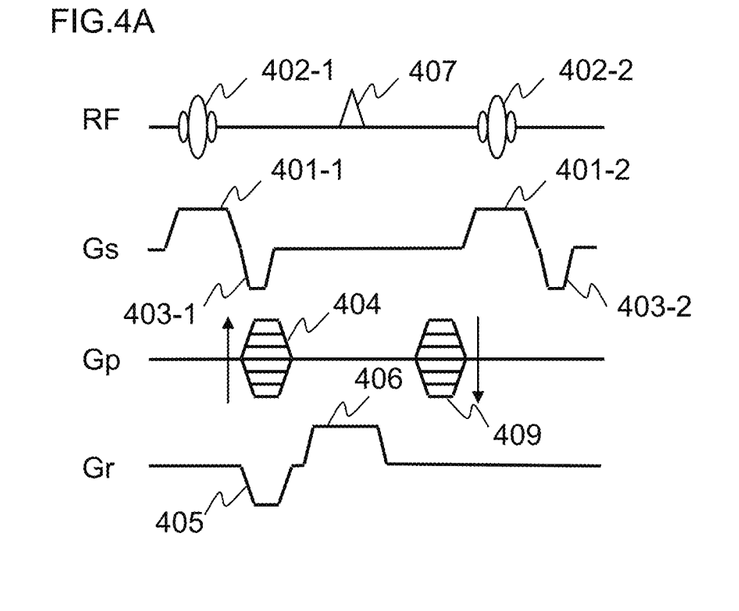
FIGS. 4A and 4B are diagrams illustrating a sequence diagram (a) and k-space data (b) according to the embodiment of the invention.

First, the signal function generation unit 222 generates a signal function 32 by numerical simulation. The signal function 32 depends on a pulse sequence usable for imaging. Here, as the pulse sequence, a GE type RF-spoiled GE sequence is used. FIG. 4A shows a timing chart representing the RF-spoiled GE sequence. In FIG. 4A, RF, Gs, Gp, and Gr represent a radio frequency magnetic field, a slice gradient magnetic field, a phase encoding gradient magnetic field, and a readout gradient magnetic field, respectively.

In the pulse sequence, first, a slice gradient magnetic field pulse 401 is applied and a radio frequency magnetic field (RF) pulse 402 is irradiated to excite magnetization of a slice in a target object. Next, a rephase gradient magnetic field pulse 403, a phase encoding gradient magnetic field pulse 404 for adding position information in a phase encoding direction to a magnetized phase, and a dephasing readout gradient magnetic field 405 are applied, and then a magnetic resonance signal (echo) 407 is measured while applying a readout gradient magnetic field pulse 406 for adding position information in a readout direction. Finally, a dephasing phase encoding gradient magnetic field pulse 409 is applied.

Figure 4B:
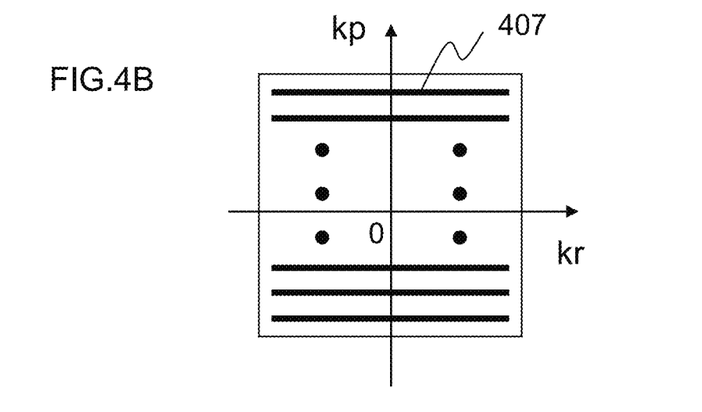

The above procedures are repeated at the repetition time TR while changing intensities (phase encoding amounts kp) of the phase encoding gradient magnetic field pulses 404, 409 and changing an RF phase by setting a phase increment value θ of the RF pulse to 117 degrees (the phase of the nth RF pulse is θ(n)=θ(n−1)+117n), and an echo necessary to obtain one image is measured. Each echo is disposed in k-space as shown in FIG. 4B, and an image is reconstructed by two-dimensional inverse Fourier transform. A pixel value of an image obtained by the imaging sequence depends on a subject parameter T1 (longitudinal relaxation time), T2 (transverse relaxation time), ρ (spin density), B1 (RF irradiation intensity), and in particular, has a characteristic that an image with emphasized T1 is obtained.

Imaging parameters that can be changed by the RF-spoiled GE are FA (flip angle), TR (repetition time), TE (echo time), and θ (RF phase increment value). Here, the RF phase increment value is generally fixed to 117 degrees so as to obtain an image contrast with less T2 dependency, which is the same as FLASH (registered trademark) as one of high-speed imaging methods. With the θ changes, the T2 dependency of the image contrast is greatly changed.

By using the above parameters, a signal function fs of the RF-spoiled GE can be expressed in Equation (1).

$$I=fs(\rho,T1,T2,B1,FA,TR,TE,\theta,Sc)=\rho Sc(T1,T2,B1\times FA,\theta,TR,TE) \quad (1)$$

Here, θ is the phase increment value of the RF pulse, and Sc is a receive coil sensitivity as the apparatus parameter. Since B1 is a coefficient of FA during imaging, B1 is in a form of a product with FA. Since ρ and Sc act as proportional coefficients with respect to signal intensity, ρ and Sc are located outside the function.

In the numerical simulation, a signal is generated by comprehensively changing the imaging parameters FA, TR, and θ with respect to optional values of the subject parameters T1 and T2 in fs, and a signal function is generated by interpolation. The spin density ρ, B1, and Sc of an imaging object are constant (for example, 1).

For example, the imaging parameters and the subject parameters change as follows. Ranges of changing parameter are set so that a range of the imaging parameters which are used for actual imaging and ranges of T1 and T2 of the subject are included therewithin.

4 TR [ms]: 10, 20, 30, 40

13 FA [degree]: 3, 5, 7, 10, 12, 15, 20, 25, 30, 35, 40, 45, 50

21 θ [degree]: from 160 degrees to 180 degrees (in 1-degree increment)

17 T2 [s]: 0.01, 0.02, 0.03, 0.04, 0.05, 0.07, 0.1, 0.14, 0.19, 0.27, 0.38, 0.53, 0.74, 1.0, 1.4, 2.0, 2.8

15 T1 [s]: 0.05, 0.07, 0.1, 0.14, 0.19, 0.27, 0.38, 0.53, 0.74, 1.0, 1.5, 2.0, 2.8, 4.0, 5.6

102,000 imaging parameter sets (310) including all combinations of the above imaging parameters and subject parameters are formed, and respective signal values are calculated by computer simulation. In the numerical simulation, a subject model in which spins are arranged on lattice points, an imaging sequence, an imaging parameter, and an apparatus parameter are input to solve a Bloch equation which is a basic equation of a magnetic resonance phenomenon, and a magnetic resonance signal is output. The subject model is given as a spatial distribution (γ, M0, T1, T2, Sc) of the spins. Here, γ is a magnetic rotation ratio, M0 is thermal equilibrium magnetization (spin density), and T1 and T2 are longitudinal relaxation time and transverse relaxation time, respectively. By reconstructing an image using the magnetic resonance signal, an image under given conditions can be obtained.

The Bloch equation is a first-order linear ordinary differential equation and is expressed by the following Equation (2).

$$\frac{d}{dt}\begin{pmatrix}M_x\\M_y\\M_z\end{pmatrix}=\begin{pmatrix}-\frac{1}{T2}&\gamma H&0\\-\gamma H&-\frac{1}{T2}&\gamma H_1\\0&-\gamma H_1&-\frac{1}{T1}\end{pmatrix}\begin{pmatrix}M_x\\M_y\\M_z\end{pmatrix}+\begin{pmatrix}0\\0\\\frac{M_0}{T1}\end{pmatrix} \quad (2)$$

$$H = B0 + G_x x + G_y y + G_z z + 2\pi\Delta f0/\gamma$$

Here, (x, y, z) represents a three-dimensional orthogonal coordinate system, and z represents a direction of a static magnetic field (the intensity is B0). (Mx, My, Mz) is a spin, Gx, Gy, and Gz are gradient magnetic field intensities in directions of x, y and z, B0 is the static magnetic field intensity, H1 is a radio frequency magnetic field intensity, and Δf0 is a frequency of a rotating coordinate system.

The signal function fs is formed by interpolation based on a signal value I obtained by the numerical simulation. In the interpolation, linear interpolation or spline interpolation of about first to third orders can be used.

Figure 5:
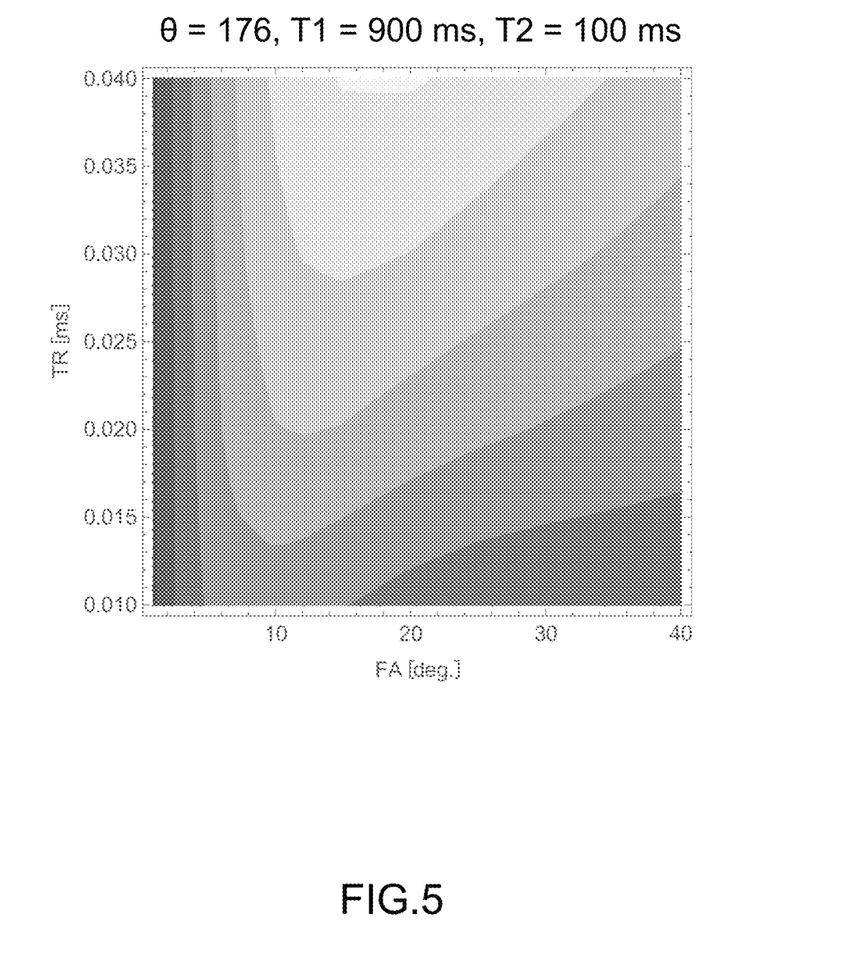
FIG. 5 is a diagram showing a part of a signal function according to the embodiment of the invention.

FIG. 5 shows a part of the intensity of the signal function generated as described above. Here, in a case where the subject parameters are T1=900 ms and T2=100 ms and the phase increment value θ=176 degrees, the horizontal axis and the vertical axis are represented as FA and TR, respectively. Once the signal function is generated and stored, it is not necessary to generate the signal function every time a calculation image is captured, and the signal function can be used repeatedly.

[S302: Imaging Condition Searching Step]

The imaging condition searching unit 225 searches for a plurality of imaging conditions (imaging parameter sets) that are used for imaging an original image using the law of error propagation.

Figure 6:
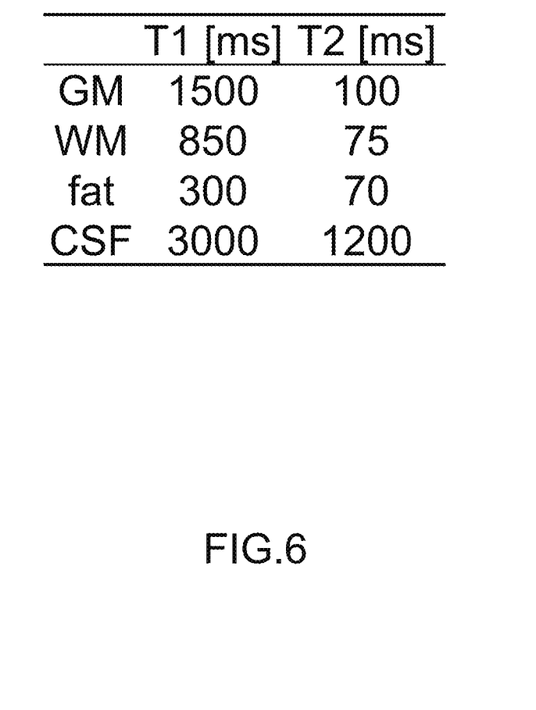
FIG. 6 shows a tissue to be optimized for an imaging parameter set, and T1 and T2 values thereof according to the embodiment of the invention.

In the present embodiment, as an example, main tissues (gray matter GM, white matter WM, fat, cerebrospinal fluid CSF) of a human head are used as objects and are optimized using the law of error propagation so as to minimize estimation errors (the magnitude of noise that is given to each image in an estimation result by the noise included in the original image) of T1, T2, B1, and "a(=ρSc)" in each map. The subject parameter values of the four tissues described above are shown in FIG. 6. When the subject parameter values are calculated as unknowns based on the signal function, since the number of unknowns is 4 (T1, T2, B1, and "a"), four or more imaging parameter sets are determined. Here, six sets of imaging parameter sets are obtained.

The value of each of the imaging parameters (FA, TR, θ) is, for example, as follows.

TR [degree]: 10, 20, 30, 40

TR [ms]: 10, 20, 30, 40

θ: from 160 degrees to 179 degrees (in 1-degree increment)

Any of the imaging parameters is combined as one set, and among a total of 320 sets (4×4×20) of combinations, a combination in which a total of six sets of TRs is within a predetermined range is searched as a search range. The reason why the total of TRs is limited is that the search range is not expanded too much and the imaging time is not extended. Specifically, the total of TRs is set from about 100 ms to 120 ms.

The search for the imaging parameter set is basically performed according to the law of error propagation as described above, but when the imaging parameter set includes an imaging parameter that causes a poor image quality of the obtained image or that is unstable, the quantitative value map may also be influenced. In the present embodiment, a processing is performed to remove an imaging parameter that deteriorates the image quality or that is unstable. A major factor why the imaging parameter deteriorates the image quality or is unstable is a variation in blood flow or cerebrospinal fluid, and the deterioration in image quality caused by the variation in flow appears as an occurrence of artifacts or a brightness variation between images in the case of continuous imaging. In the present embodiment, for each imaging condition, the brightness variation between images is examined in advance, and an imaging parameter set that does not cause the brightness variation between the images is determined. By using the brightness variation, the deterioration in image quality that may not clearly appear as artifacts or the deterioration in image quality that may not be visually observed can be evaluated, and the evaluation of the image quality can be easily automated.

Figure 7:
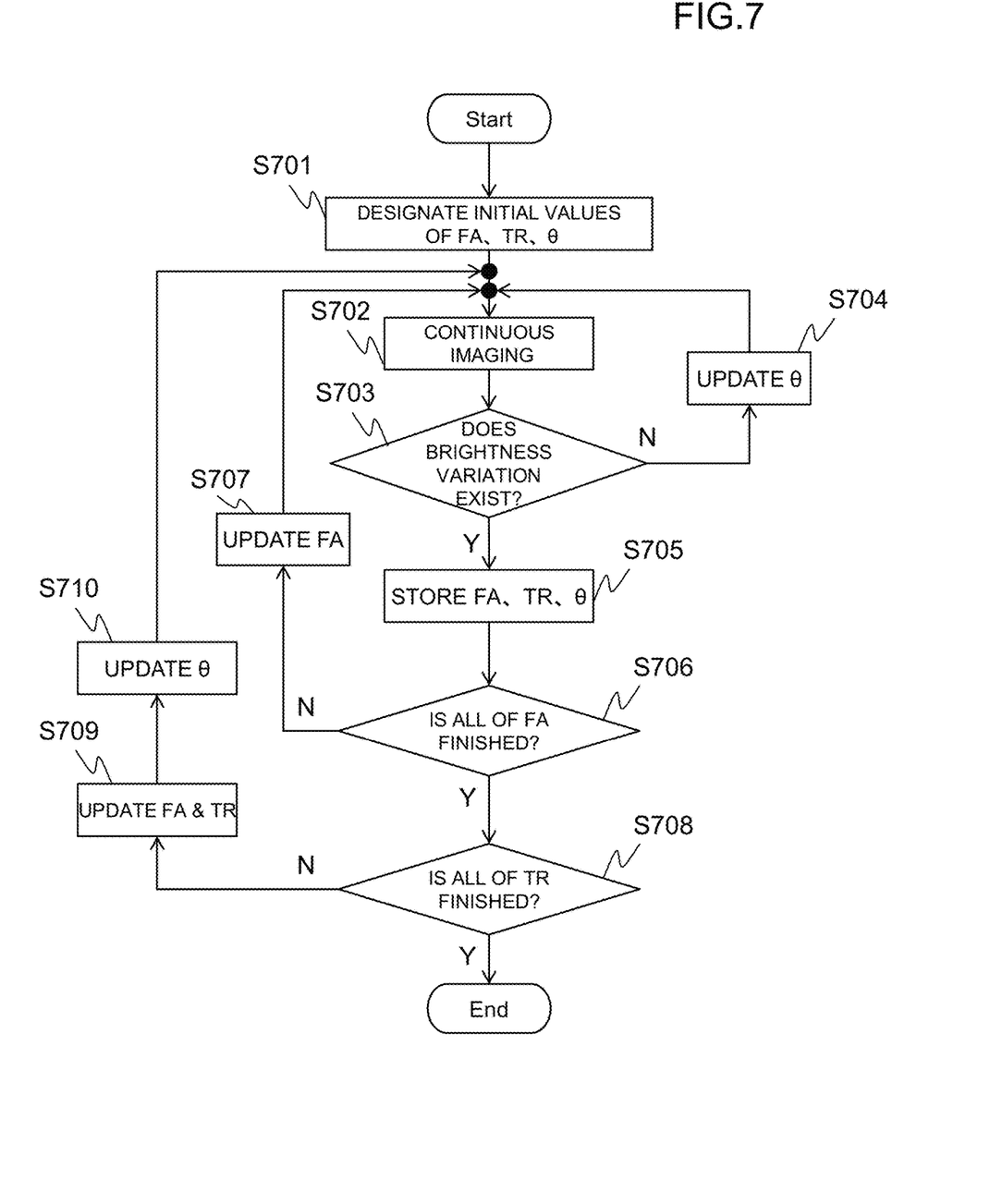
FIG. 7 is a processing flow showing details of an imaging parameter searching processing.

A processing flow performed before searching for the imaging parameter set will be described with reference to the flow shown in FIG. 7. Here, of the three imaging parameters (FA, TR, θ), θ at which the image quality is stabilized is determined for each of FA and TR. In general, it is known that, for each imaging parameter, the shorter the TR is, the more likely the image is influenced by the flow, and the smaller the FA is, the less likely the image is influenced by the flow. Furthermore, the closer the θ is to 180 degrees, the higher the contrast of the region in which the flow is present and, therefore, the image is easily influenced by the flow. In the present embodiment, based on the above knowledge, first, FA and TR at which the brightness variation is most difficult to occur are designated as initial values, θ is set to an initial value close to 180 degrees, and a search is performed to sequentially determine allowable θ (S701). In one example, as the initial values, FA is set to the minimum value of 10 degrees, and TR and θ are set to the maximum values of 40 ms and 179 degrees, respectively.

Figure 8:
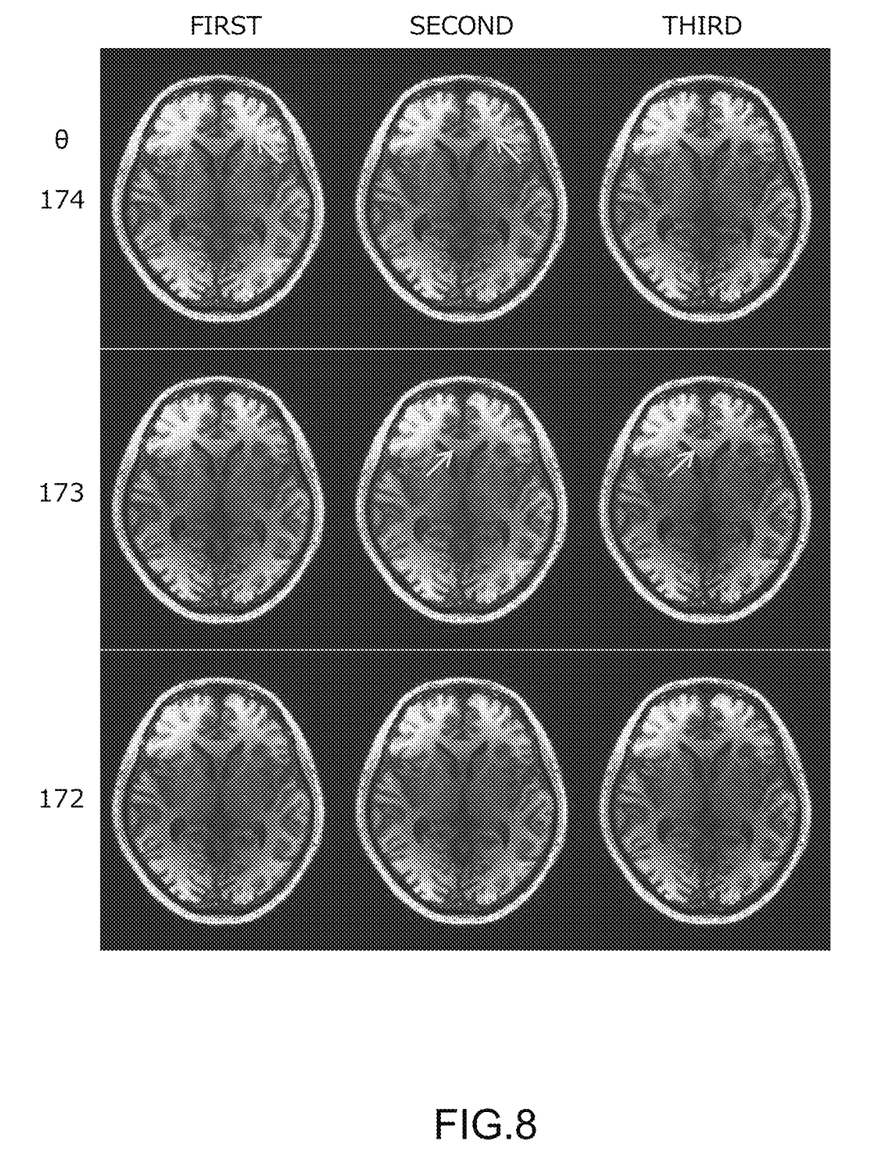
FIG. 8 is a diagram illustrating a difference in image quality depending on imaging conditions according to the embodiment of the invention.
Figure 9A:
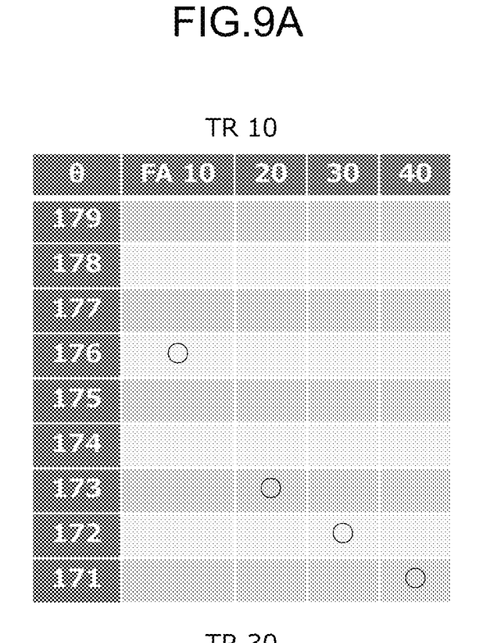
FIGS. 9A-9D show respective diagrams illustrating imaging condition searching according to the embodiment of the invention.
Figure 9B:
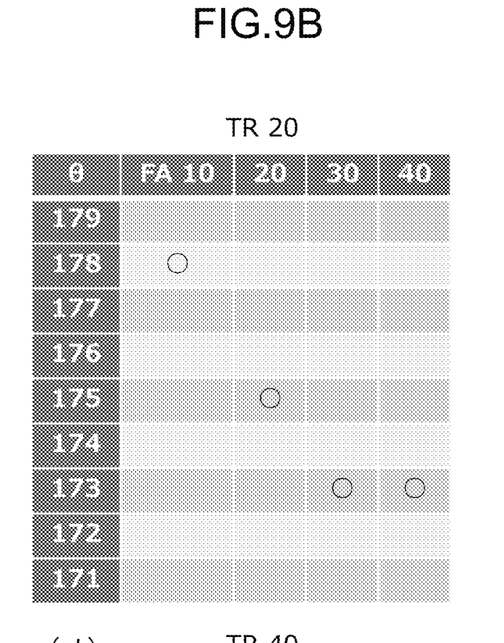
Figure 9C:
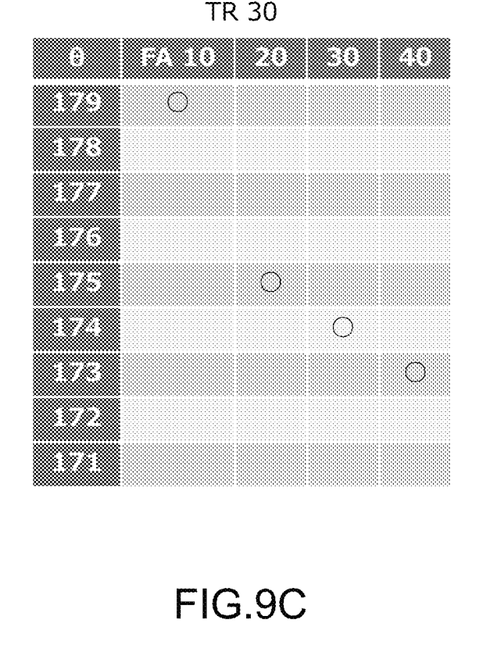
Figure 9D:
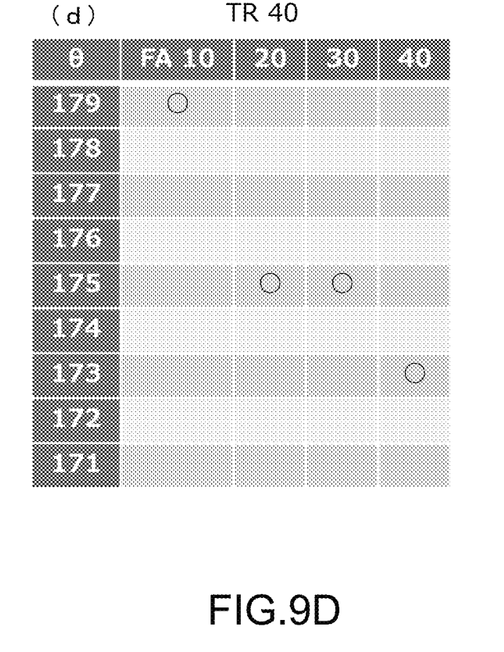

Under the above condition, the subject is continuously imaged (S702). The number of times of imaging may be at least twice as long as the brightness variation can be determined, and may be three or more times if possible. Then, as shown in FIG. 8, it is evaluated whether a brightness variation occurs in the images continuously imaged (S703). The evaluation of the brightness variation can be performed by visual observation. Alternatively, when the evaluation is automatically performed, a difference between a first image and a second and subsequent images of the images continuously imaged may be calculated, and when the variation is several percent (for example, 5%) or less, it may be determined that substantially no brightness variation occurs. The difference may be a simple difference between pixel values, or, for example, a root mean squared error (RMSE) is calculated.

FIG. 8 is a diagram showing reconstructed images obtained by varying θ to 174 degrees, 173 degrees, and 172 degrees and performing three continuous imaging operations when FA is 30 degrees and TR is 20 ms. When θ is 174 degrees and 173 degrees, the brightness varied, bright or dark, between the images as indicated by white arrows in the diagram. The main reason for the brightness variation is a variation in blood flow or cerebrospinal fluid. In contrast, when θ is 172 degrees, it can be seen that no such a variation occurs and the imaging parameter set is that of less likely to be influenced by the flow.

When it is determined in step S703 that the brightness variation occurs, θ is updated (S704), and the continuous imaging and the evaluation of the brightness variation are repeated in the same manner. Here, since the initial value of θ is set to the maximum value (179 degrees), θ is decreased by 1 degree for each update. The step is repeated until no brightness variation occurs, and θ at which no brightness variation occurs is stored together with FA and TR (S705).

Next, FA is updated to 20 degrees (S706, S707), the continuous imaging (S702) and the brightness variation determination (S703) are repeated in the same manner as described above, and θ at which no brightness variation occurs is stored together with FA and TR (S705). When FA is updated, θ may be remained in the value immediately before the FA update without returning to the initial value (10 degrees). As a reason, for example, when FA is 10 degrees or 20 degrees, the brightness variation is more likely to occur at 20 degrees, and therefore, θ at which no brightness variation occurs when FA is set to 20 degrees, will be equal to or smaller than that in the case where FA is 10 degrees.

When the evaluation for all FA is completed in this way (S706), TR is updated to a small value (30 ms), and FA is returned to the minimum value of 10 degrees (S709). θ is updated to a value of θ at which it is determined that no brightness variation occurs at TR before the update and the minimum FA of 10 degrees. As a reason, the smaller the TR is, the more likely the brightness variation is to occur, and therefore, θ at which no brightness variation occurs when the TR is updated to a small value will be equal to or smaller than θ before the TR update. Next, the evaluation of the brightness variation is repeated in the same manner as described above.

When the above step is repeated and all TR are updated, the processing is completed (S708). By the processing, the imaging parameter at which the brightness variation occurs can be excluded before the combination of the imaging parameter sets is optimized using the law of error propagation.

FIG. 9 show examples of combinations of imaging parameter sets at which it is determined, by the above processing, that no brightness variation occurs. In FIG. 9, (a) to (d) are diagrams showing the imaging parameter sets selected (stored) in step S705 when TR is 10 ms, 20 ms, 30 ms, and 40 ms, in which "○" indicates the stored imaging parameter set, and an imaging parameter set having a value of θ smaller than "○" is an imaging parameter set at which no brightness variation occurs. That is, when the maximum θ at which it is determined that no brightness variation occurs at the predetermined FA and TR is obtained in the above processing, the evaluation of the brightness variation at the same FA and TR can be omitted.

Next, from all combinations of FA, TR, and θ that satisfy the limitation of the total of TRs (here, 120 ms or less), a condition having the brightness variation is removed in advance (after θ larger than θ marked with "○" in FIG. 9 is removed) as described above, and then for the remaining imaging parameter sets, an imaging parameter set 33 for obtaining a calculation image is determined according to the law of error propagation by using the signal function 32 obtained in advance.

As described above, the number of imaging parameter sets needs to be equal to or greater than the number of unknowns. As an example, provided that four parameters, i.e., the subject parameters T1, T2, and B1, and a (=ρSc), which is the product of ρ and the apparatus parameter Sc, are estimated, the following six sets of imaging parameter sets (FA, TR, and θ) are determined.
(40, 40, 173), (10, 30, 177), (40, 20, 160), (40, 10, 162), (40, 10, 162), (40, 10, 162)

Among the six imaging parameter sets, four imaging parameter sets have different combinations of parameter values, and the remaining two imaging parameter sets are the same as one of the four imaging parameter sets. Obtained images with the same imaging parameter sets are added for using. That is, an imaging parameter which is presumed to have a low SN, among the imaging parameters, may be repeated to improve SN so long as a condition that different imaging parameter sets are equal to or greater than the unknowns is satisfied.

[S303: Echo Measurement]

The measurement unit 110 sets the imaging sequence in the sequencer 104 according to the predetermined pulse sequence and the imaging parameter set 33 determined by the imaging condition determination unit 224, and measures echo signals. Next, the measured echo signals are arranged in the k-space to obtain measurement data (k-space data) 34.

[S304: Image Reconstruction]

The image reconstruction unit 221 performs inverse Fourier transform on the measurement data collected by the measurement unit 110 and reconstructs an image. Accordingly, six reconstructed images (original images) 35 imaged under six imaging parameter sets are obtained.

[S305, S306: Parameter Estimation and Map Generation]

The parameter estimation unit 223 estimates the subject parameter and the apparatus parameter by using the six original images 35 and the signal function 32. Specifically, by fitting a signal value I for each pixel to a function f of Equation (3) obtained by modifying Equation (1), the four parameters T1, T2, B1, and a (ρ×Sc) are estimated.

$$I = af(T1, T2, \theta, B1 \times FA, TR) \quad (3)$$

$$a = \rho Sc$$

The function fitting is performed by a least squares method represented by Equation (4).

$$x^2 = \Sigma_{FA,\Delta\theta,TR}\{(FA,\theta,TR) - af(T1,T2,\theta,B1\times FA,TR)\} = \min \quad (4)$$

Here, x is a sum of residuals of the signal function and pixel values of a phantom, and I is a pixel value in the reconstructed image (original image) obtained by imaging under the imaging parameters (FA, TR, θ) described above. By performing the calculation for each pixel, a calculation image (parameter map) having the same matrix size as that of the reconstructed image can be generated. For the calculation image, four types of T1, T2, B1, and ρSc can be generated. A new calculation image may be generated by calculation between calculation images.

[S307: Image Display]

The calculation image is displayed on the display 120 as necessary.

Figure 10A:
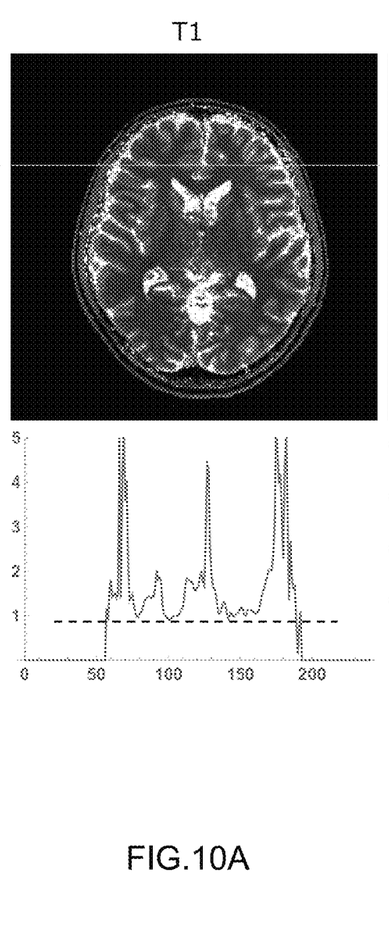
FIGS. 10A and 10B are diagrams illustrating an image quality improvement effect of a map according to the embodiment of the invention.
Figure 10B:
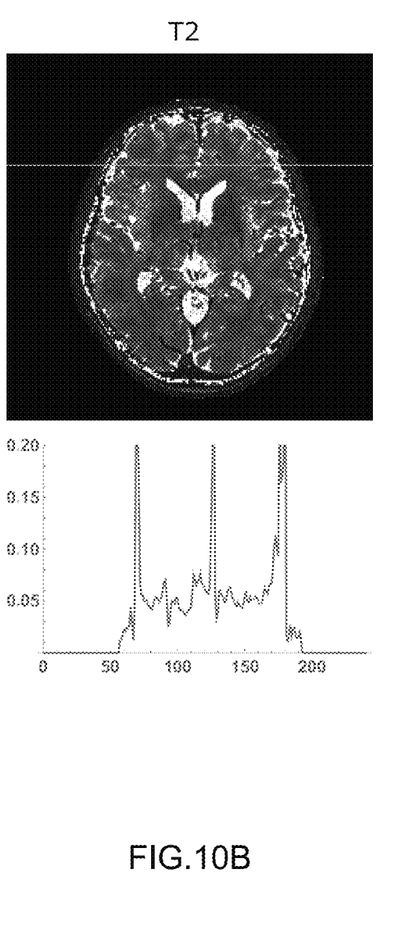
Figure 11A:
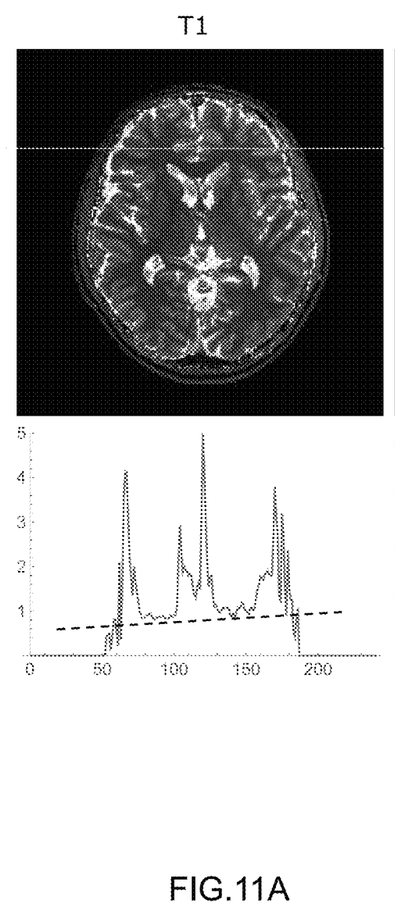
FIGS. 11A and 11B are diagrams illustrating an image quality improvement effect of a map according to the embodiment of the invention.
Figure 11B:
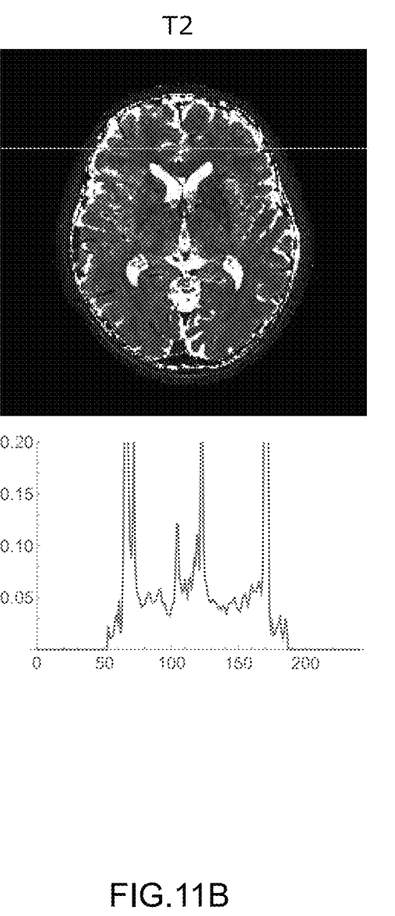

An example of T1 and T2 maps of the head of a healthy person estimated in the above manner is shown in FIGS. 10A and 10B. FIGS. 11A and 11B show T1 and T2 maps generated by performing imaging using imaging parameter sets searched without excluding an imaging condition causing a poor image quality for comparison. In FIGS. 10A and 10B, and FIGS. 11A and 11B, FIG. 10A and FIG. 11A are T1 maps, FIG. 10B and FIG. 11B are T2 maps, and the lower part of each map is a profile of a straight line (front head) shown in the image in the upper part.

In the T1 map shown in FIG. 11A, values of a frontal white matter portion are different on the left and right, whereas in the T1 map shown in FIG. 10A, values of the frontal white matter portion on the left and right are the same, indicating that an original image having an unstable brightness is not included. When the T2 maps are compared, the noise in the vicinity of the center of the map is smaller in FIG. 10B, and a jagged profile is also smaller in FIG. 10B. This is also an effect of excluding an original image with a poor image quality.

Modification

In the present embodiment, a case where the image quality deteriorates by the cerebrospinal fluid CSF has been described using a brain image as an example of an image with a poor image quality. Alternatively, the effect of the blood flow on joints such as a shoulder joint and a knee joint, and the effect of the flow and body motion on the image quality are also different depending on the imaging conditions for portions that are easily influenced by breathing and pulsation (such as chest). For these portions, an imaging parameter set causing a poor image quality can be removed from the imaging parameter sets by the same method as the above-described method (for example, the procedure in FIG. 7), and the same effect can be obtained.

In the present embodiment, a case has been described in which the continuous imaging is performed and the imaging parameter set to be excluded from a plurality of obtained images is automatically determined based on the brightness variation. Alternatively, artifacts that can be observed on an image may occur due to a portion, a flow, or a body motion, and in such a case, the presence or absence of the artifacts may be determined on the image. The determination of the presence or absence of the artifacts may be visually observed by a user, or may be performed by comparing the image with an image captured under an imaging condition that is known to be a condition generating no flow artifacts.

In the present embodiment, a combination of three parameters FA, TR, and θ has been described as the imaging parameter set. Alternatively, it is possible to make various changes such as further addition of another imaging parameter (for example, TE) and searching for an imaging parameter set to be excluded by fixing one (for example, TR) of the above three parameters and changing only other parameters.

In the above embodiment, regarding the signal function, a case where the signal function of the GE-type RF-spoiled GE sequence is obtained by the numerical simulation has been described. Alternatively, when the imaging sequence is a sequence in which the signal function is obtained by numerical calculation, step S301 in FIG. 3 can be omitted.

As described above, according to the present embodiment and the modification thereof, when a plurality of original images are obtained by performing a plurality of times of imaging to estimate a parameter, a plurality of imaging parameters can be appropriately set, and accordingly, it is possible to prevent an image with a poor image quality due to the influence of a flow or the like from being included in the original images, and it is possible to stably perform the parameter estimation and the map generation with reliability. According to the present embodiment, when the imaging parameter sets are optimized according to the law of error propagation, it is possible to reduce the amount of the computation related to the optimization by limiting the range of the imaging parameter sets to be searched.

What is claimed is:

1. A magnetic resonance imaging apparatus, comprising:
    a measurement unit configured to measure, in accordance with a specific imaging condition of a predetermined imaging sequence, an echo signal generated from a subject placed in a static magnetic field by applying a radio frequency magnetic field and a gradient magnetic field to the subject;
    an image reconstruction unit configured to generate a reconstructed image based on the measured echo signal;
    a parameter estimation unit configured to estimate (a) a distribution of quantitative values of magnetic resonance corresponding to subject parameters that vary depending on the subject or (b) a distribution of apparatus parameters that vary depending on the apparatus, by using (i) reconstructed images obtained by executing the imaging sequence, while changing the specific imaging condition, and (ii) a signal function determined by the imaging sequence; and
    an imaging condition determination unit configured to determine plural combinations of imaging conditions for obtaining a plurality of reconstructed images to be used by the parameter estimation unit, and configured to evaluate an image quality of the reconstructed image,
    the imaging condition determination unit including an imaging condition searching unit configured to search for a combination of imaging conditions to be excluded, in view of brightness variation therefrom, from the plural combinations of imaging conditions, and configured to exclude the combination of imaging conditions to be excluded, in view of the brightness variation therefrom, from the plural combinations of imaging conditions to be used.

2. The magnetic resonance imaging apparatus according to claim 1, wherein
    the imaging condition determination unit is configured to determine, based on the amount of artifacts occurring in a reconstructed image, the imaging conditions necessary for parameter estimation.

3. The magnetic resonance imaging apparatus according to claim 1, wherein the imaging condition determination unit is configured to evaluate a brightness variation between reconstructed images obtained by performing imaging a plurality of times under the same imaging condition, and determine, based on a result, the imaging conditions necessary for parameter estimation.

4. The magnetic resonance imaging apparatus according to claim 3, wherein
the imaging condition determination unit is configured to evaluate the brightness variation based on a difference or a root mean squared error between the reconstructed images.

5. The magnetic resonance imaging apparatus according to claim 1, wherein
the imaging conditions determined by the imaging condition determination unit are a combination of a repetition time (TR) of the imaging sequence, a flip angle (FA) of the radio frequency magnetic field, and a phase increment value (θ) of the radio frequency magnetic field.

6. The magnetic resonance imaging apparatus according to claim 5, wherein
the imaging condition determination unit is configured to determine, in a predetermined repetition time (TR) and a predetermined flip angle (FA), a phase increment value (θ) of the radio frequency magnetic field at the repetition time and the flip angle based on a brightness variation between reconstructed images obtained by performing imaging a plurality of times under the same imaging condition.

7. The magnetic resonance imaging apparatus according to claim 5, wherein
the imaging condition determination unit is configured to determine, as the combinations of imaging conditions, combinations having a number equal to or more than the number of parameters estimated by the parameter estimation unit.

8. The magnetic resonance imaging apparatus according to claim 7, wherein
the combinations determined by the imaging condition determination unit include the same combination.

9. An image processing method, performed by a magnetic resonance imaging apparatus, of processing a plurality of reconstructed images obtained under different specific imaging conditions in the magnetic resonance imaging apparatus and estimating a distribution of quantitative values of magnetic resonance corresponding to subject parameters that vary depending on a subject or a distribution of apparatus parameters that vary depending on the apparatus, the image processing method comprising:
evaluating an image quality of a reconstructed image under each imaging condition; and
searching for an imaging condition to be used for estimation of the distribution to be performed; and
searching for a combination of imaging conditions to be excluded, in view of brightness variation therefrom, from the imaging condition to be used, and determining the imaging condition to be used while excluding the combination of imaging conditions to be excluded in view of the brightness variation therefrom.

10. The image processing method according to claim 9, wherein
searching for the imaging condition includes evaluating artifacts caused by flow or a body motion in the reconstructed image, and determining an imaging condition with fewer artifacts in the reconstructed image as the imaging condition to be used for the estimation of the distribution.

11. The image processing method according to claim 10, wherein
searching for the imaging condition includes evaluating the artifacts based on a brightness variation between reconstructed images obtained by performing imaging a plurality of times under the same imaging condition.

* * * * *